(12) United States Patent
Gaiba et al.

(10) Patent No.: US 6,987,119 B2
(45) Date of Patent: Jan. 17, 2006

(54) IMIDAZOL-2-CARBOXAMIDE DERIVATIVES AS RAF KINASE INHIBITORS

(75) Inventors: Alessandra Gaiba, London (GB); Andrew Kenneth Takle, Great Dunmow (GB); David Matthew Wilson, Herts (GB)

(73) Assignee: SmithKline Beecham P.L.C., Brentford (GB)

( * ) Notice: Subject to any disclaimer, the term of this patent is extended or adjusted under 35 U.S.C. 154(b) by 0 days.

(21) Appl. No.: 10/220,675

(22) PCT Filed: Mar. 2, 2001

(86) PCT No.: PCT/GB01/00916

§ 371 (c)(1),
(2), (4) Date: Dec. 18, 2002

(87) PCT Pub. No.: WO01/66540

PCT Pub. Date: Sep. 13, 2001

(65) Prior Publication Data

US 2003/0134837 A1 Jul. 17, 2003

(30) Foreign Application Priority Data

Mar. 6, 2000 (GB) ............................................. 0005357

(51) Int. Cl.
*A61K 31/44* (2006.01)
*C07D 401/04* (2006.01)

(52) U.S. Cl. .................... 514/341; 546/274.7; 544/242; 544/297

(58) Field of Classification Search .............. 546/274.7; 514/341; 544/242, 297
See application file for complete search history.

(56) References Cited

U.S. PATENT DOCUMENTS

| | | | |
|---|---|---|---|
| 4,447,431 | A | 5/1984 | Sallman |
| 5,236,917 | A | 8/1993 | Dunlap et al. |
| 5,514,505 | A | 5/1996 | Limburg et al. |
| 5,717,100 | A | 2/1998 | Selnick et al. |
| 5,859,041 | A | 1/1999 | Liverton et al. |

FOREIGN PATENT DOCUMENTS

| | | |
|---|---|---|
| GB | 2 306 108 | 4/1994 |
| WO | WO96/03387 | 2/1996 |
| WO | WO96/41645 | 12/1996 |
| WO | WO 97/12876 | 4/1997 |
| WO | WO 99/32436 | 4/1997 |
| WO | WO97/36587 | 10/1997 |
| WO | WO97/47618 | 12/1997 |
| WO | WO98/16227 | 4/1998 |
| WO | WO 99/03837 | 1/1999 |
| WO | WO99/21555 | 5/1999 |
| WO | WO 99/61437 | 12/1999 |
| WO | WO 01/37835 | 5/2001 |
| WO | WO 02/39954 | 5/2002 |

OTHER PUBLICATIONS

Liverton, N.J et al: Design and Synthesis of Potent, Selective and Orally Bioavailable tetrasubstituted Imidazoles of p38 Mitogen Activated Protein Kinase. J. Med Chem 1999 42 2180–2190.

Lisnock, J et al: Molecular Basis for p38 Protein Kinase Inhibitor Specificity, BioChemistry, 1998, 37, 16573–16581.

Toledo L.M et al, The Structure–Based Design of ATP–site Directed Protein Kinase Inhibitors, Current Medicinal Chemistry 1999, 6, 775–805.

Stover D.R et al, Recent Advances in protein Kinase inhibition:Current molecular scaffolds used for inhibitor synthesis. Current Opinion in Drug Discovery and Development 1999 2(4) 274–285.

Salituro F.G, et al Inhibitors of p38 MAP Kinase: Therapeutic Intervention in Cytokine–Mediated Disease, Current Medicinal Chemistry 1999, 6, 807–823.

(Continued)

*Primary Examiner*—Golam M M Shameem
(74) *Attorney, Agent, or Firm*—Grace C. Hsu; Mary McCarthy; Charles M. Kinzig

(57) ABSTRACT

Compounds of formula (I):

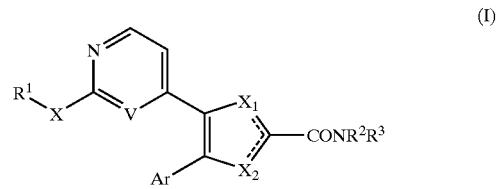

wherein X is O, $CH_2$, S or NH, or the moiety X—$R^1$ is hydrogen;

V is CH or N;

$R^1$ is hydrogen, $C_{1-6}$alkyl, $C_{3-7}$cycloalkyl, aryl, aryl$C_{1-6}$alkyl, heterocyclyl, heterocyclyl-$C_{1-6}$alkyl, heteroaryl, or heteroaryl$C_{1-6}$alkyl any of which except hydrogen may be optionally substituted;

$R^2$ and $R^3$ independently represent hydrogen, $C_{1-6}$alkyl, $C_{3-7}$cycloalkyl, aryl, aryl$C_{1-6}$alkyl, heteroaryl, heteroaryl$C_{1-6}$alkyl, heterocyclyl, or heterocyclyl$C_{1-6}$alkyl any one of which except hydrogen may be optionally substituted, or $R^2$ and $R^3$ together with the nitrogen atom to which they are attached form a 4- to 10-membered optionally substituted monocyclic or bicyclic ring;

Ar is an aryl or heteroaryl ring either of which may be optionally substituted;

one of $X_1$ and $X_2$ is N and the other is $NR^4$, wherein $R^4$ is hydrogen, $C_{1-6}$alkyl, or aryl$C_{1-6}$alkyl;

or pharmaceutically acceptable salts thereof; their use as inhibitors of Raf kinases and pharmaceutical compositions containing them.

9 Claims, No Drawings

OTHER PUBLICATIONS

Adams J.L. et al, Recent progress towards the idnetification of selective inhibitors of serine/theronine protein kinases, Current Opinion in Drug Discovery and Development 1999 2(2) 96–109.

Hall–Jackson C.A. et al, Effect of SB2030580 on the activity of c–Raf in vitro and and in vivo Oncogene (1999) 18, 2047–2054.

Boehm J. C. et al, New Inhibitors of p38 Kinase, Exp Opinion Ther Patents (2000) 10 (1).

Garcia–Echeverria C. et al, ATP Site Directed Competitive and Irreversible Inhibitors of Protein Kinase, Med Res Reviews 2000, 20(1), 28–57.

Wang Z et al, Structural basis of inhibitor selectivity in MAP Kinases, Structure Sep. 15, 1998, 6: 1117–1128.

Lackey K et al, The Discovery of Potent cRaf 1 Kinase Inhibitors, Bioorganic & Medical Chemistry Letters 10 (2000) 223–226.

Adams. J.L et al, Pyrimidinylimidazole Inhibitors of CSBP/p38 Demonstrating Decreased inhibition of Hepatic Cytochrome p450 Enzymes, Bioorganic & Medical Chemistry Letters 8 (1998) 3111–3116.

Gallagher T.F et al, Regulation of Stress–Induced Cytokine Production by Pyridinylimidazole: Inhibition of CSBP Kinase; Bioorganic & Medical Chemistry vol. 5 No. 1 pp 49–64 1997.

Boehm J. C. et al, 1–Substituted 4–Aryl–5–pyridinylimidazoles: A new class of cytokine suppressive drugs with low 5–Lipoxygenase and cycloxygenase inhibitory potency, J. Med Chem 1996, 39 3929–3937.

Cuenda A. et al, SB203580 is a specific inhibitor of a MAP Kinase homologue which is stimulated by cellular stresses and interleukin–1, FEBS Letters 364 (1995) 229–233.

Lee J. C. et al, p 38 Mitogen–Activated Protein Kinase Inhibitors–Mechanisms and Therapeutic Potentials, Pharmacol Ther. vol. 82. Nos 2–3 pp 389–397, 1999.

Young P. R. et al, Pyridinyl Imidazole Inhibitors of p38 Mitogen–activated Protein Kinase bind in the ATP site, The Journal of Biological Chemistry vol. 272 No. 18 Issue of May 2 pp 12116–12121 1997.

Dumas J. et al, Discovery of a new class of p38 Kinase inhibitors, Bioorganic & Medical Chemistry Letters 10 (2000) 2047–2050.

Dumas J, et al, 1–Phenyl–5–pyrazolyl Ureas Potent and Selective p38 Kinase Inhibitors, Bioorganic & Medical Chemistry Letters 10 (2000) 2051–2054.

Revesz L, et al, SAR of 4–Hydroxypiperidine and Hydroxyalkyl Substituted Heterocycles as Novel p38 Map Kinase Inhibitors, Bioorganic & Medical Chemistry Letters 10(2000) 1261–1264.

Laszlo S.E, et al, Pyrroles and other heterocycles as inhibitors of p38 Kinase, Bioorganic & Medical Chemistry Letters 8 (1998) 2689–2694.

Tong L. et, A highly specific inhibitor of human p38 MAP Kinase binds in the ATP pocket, Nature Structural Biology vol. 4 No. 4 Apr. 1997 p 311.

p38 Inhibitors based on pyridylurea and pyridylacetoamide templates, Exp Opin. Ther. Patents (2000) 10(7) 1151–1154.

Two Novel structural classes of p38 Kinase inhibitors, Exp Opin. Ther. Patents (1999) 9(4) 477–480.

Henry. J R., et al, Potent Inhibitors of the Map Kinase p38, Bioorganic & Medical Chemistry Letters 8 (1998) 3335–3340.

Henry. J. R., et al, p38 mitogen–activated protein kinase as a target for drug discovery, Drugs of the Future 1999, 24 (12) 1345–1354.

Lowinger, T.B. et al, Discovery of a novel class of potent BRaf kinase inhibitors: Strucutre activity relationships 335 Clinical Cancer Research vol. 6 Nov. 2000 (Supplement) Poster session 13 4533.

Eberwein D, et al, In vivo activity of a Raf kinase inhibitor in human tumor xenograft models, 406 Clinical Cancer Research vol. 6 Nov. 2000 (Supplement) Poster session 17 4547.

Claiborne C.F. et al, An efficient sythesis of Tertasubstituted Imidazoles from N–(2–Oxo)–amides, Tetrahedron Letters 39, (1998) 8939–3942.

Antolini M et al, Analogues of 4,5–bis(3, 5–Dichlorophenyl)–2–trifluoromethyl–1H–Imidazole as Potential Antibacterial Agents. Bioorganic & Medical Chemistry Letters 9 (1999) 1023–1028.

Bilodeau M. T. et al, Solid–supported synthesis of Imidazoles: A Strategy for direct resin–attachment to the Imidazole Core. J. Org. Chem 1998 63. 2800–2801.

Astles P.C. et al, Acyl–CoA:Cholesterol O–Acyltransferase (ACAT) Inhibitors.2.2–(1,3–Dioxan–2–yl)–4, 5–diphenyl–1H–imidazoles as Potent Inhibitors of ACAT, J. Med. Chem. 1996, 39, 1423.

Heimbrock, D.C. et al; Identification of Potent, Selective Inhibitors of Raf Protein Kinase, Amer. Assoc for Cancer Res New Orleans Apr. 1998.

Liverton, N.J. et al: Design and Synthesis of Potent, Selective and Orally Bioavailable tetrasubstituted Imidazoles of p38 Mitogen Activated Protein Kinase. J. Med Chem 1999 42 2180–2190.

Lisnock, J et al: Molecular Basis for p38 Protein Kinase Inhibitor Specificity, BioChemistry, 1998, 37, 16573–16581.

Toledo L., et al, The Structure–Based Design of ATP–site Directed Protein Kinase Inhibitors, Current Medicinal Chemistry 1999, 6, 775–805.

Stover D.R et al, Recent Advances in protein Kinase inhibition: Current molecular scaffolds used for inhibitor synthesis. Current Opinion in Drug Discovery and Development 1999 2(4) 274–285.

Salituro F.G, et al, Inhibitors of p38 MAP Kinase: Therapeutic Intervention in Cytokine–Mediated Disease, Current Medicinal Chemistry 1999, 6, 807–823.

Adams J.L. et al, Recent progress towards the idnetification of selective inhibitors of serine/theronine protein kinases, Current Opinion in Drug Discovery and Development 1999 2(2) 96–109.

Hall–Jackson C.A. et al, Effect of SB203580 on the activity of c–Raf in vitro and in vivo Oncogene (1999) 18, 2047–2054.

Boehm J. C. et al, New inhibitors of p38 Kinase, Exp Opinion Ther Patents (2000) 10 (1).

Garcia–Echeverria C. et al, ATP Site Directed Competitive and Irreversible Inhibitors of Protein Kinase, Med Res Reviews 2000, 20(1), 28–57.

Wang Z et al, Structural basis of inhibitor selectivity in MAP Kinases, Stucture Sep. 15, 1998, 6: 1117–1128.

Laekey K et al, The Discovery of Potent cRaf1 Kinase Inhibitors, Bioorganic & Medical Chemistry Letters 10 (2000) 223–226.

Adams. et al, Pyrimidinylimidazole Inhibitors of CSBP/p38 Demonstrating Decreased inhibition of Hepatic Cytochrome p450 Enzymes, Bioorganic & Medical Chemistry Letters 8 (1998) 3111–3116.

Gallagher T.F et al, Regulation of Stress–Induced Cytokine Production by Pyridinylimidazole: Inhibition of CSBP Kinase; Bioorganic & Medical Chemistry vol. 5 No. 1 pp. 49–64 1997.

Boehm J. C. et al, 1–Substituted 4–Aryl–5–pyridinylimidazoles: A new class of cytokine suppressive drugs with low 5–Lipoxygenase and cylcoxygenase inhibitory potency, J. Med Chem 1996, 39 3929–3937.

Cuenda A. et al, SB203580 is a specific inhibitor of a MAP Kinase homologue which is stimulated by cellular stresses and interleukin–1, FEBS Letters 364 (1995) 229–233.

Lee J. C. et al, p 38 Mitogen–Activtated Protein Kinase Inhibitors –Mechanisms and Therapeutics Potentials, Pharmacol Ther. vol. 82. Nos. 2–3 pp. 389–397, 1999.

Young P. R. et al, Pyridinyl Imidazole Inhibitors of p38 Mitogen–activated Protein Kinase bind in the ATP site, The Journal of Biological Chemistry vol. 272 No. 18 Issue of May 2 pp. 12116–12121 1997.

Dumas J, et al, Discovery of a new class of p38 Kinase Inhibitors, Bioorganic & Medical Chemistry Letters 10 (2000) 2047–2050.

Dumas, J, et al, 1–Phenyl–5–pyrazolyl Ureas Potent and Selective p38 Kinase Inhibitors, Bioorganic & Medical Chemistry Letters 10 (2000) 2051–2054.

Revesz L, et al, SAR of 4–Hydroxypiperidine and Hydroxyalkyl Substituted Heterocycles as Novel p38 Map Kinase Inhibitors, Bioorganic & Medical Chemistry Letters 10 (2000) 1261–1264.

Laszlo S.E, et al, Pyrroles and other heterocycles as inhibitors of p38 Kinase, Bioorganic & Medical Chemistry Letters 8 (1998) 2689–2694.

Tong L. et al, A highly specific inhibitor of human p38 MAP Kinase binds in the ATP pocket, Nature Structural Biology vol. 4 No. 4 Apr. 1997 p. 311.

p38 Inhibitors based on pyridylurea and pyridylacetoamide templates, Exp Opin. Ther. Patents (2000) 20 (7) 1151–1154.

Two Novel structural classes of p38 Kinase inhibitors, Exp Opin. Ther. Patents (1999) 9 (4) 477–480.

Henry J. R., et al, Potent inhibitors of the Map Kinase p38, Bioorganic & Medical Chemistry Letters 8 (1998) 3335–3340.

Henry. J. R., et al, p38 mitogen–activated protein kinase as a target for drug discovery, Drugs of the Future 1999, 24, (12) 1345–1354.

Lowinger, T.B. et al, Discovery of a novel class of potent BRaf kinase inhibitors: Structure activity relationships 335 Clinical Cancer Research vol. 6 Nov. 2000 (Supplement) Poster session 13 4533.

Eberwein D, et al, In vivo activity of a Raf kinase inhibitor in human tumor xenograft models, 406 Clinical Cancer Research vol. 6 Nov. 2000 (Supplement) Poster session 17 4547.

Claiborne C.F. et al, An efficient sythesis of Tertasubstituted Imidazoles from N–(2–Oxo)–amides, Tetrahedron Letters 39, (1998) 8939–8942.

Antolini M et al, Analogues of 4,5–bis(3, 5–Dichlorophenyl)–2–trifluoromethyl–1H–Imidazole as Potential Antibacterial Agents. Bioorganic & Medical Chemistry Letters 9 (1999) 1023–1028.

Bilodeau M. T. et al, Solid–supported synthesis of Imidazoles: A Strategy for direct resin–attachment to the Imidazole Core. J. Org. Chem 1998 63. 2800–2801.

Astles P.C. et al, Acyl–CoA:Cholesterol O–Acyltransferase (ACAT) Inhibitors.2.2–(1,3–Dioxan–2–yl)–4, 5–diphenyl–1H–imidazoles as Potent Inhibitors of ACAT, J.Med.Chem. 1996, 39, 1423.

IMIDAZOL-2-CARBOXAMIDE DERIVATIVES AS RAF KINASE INHIBITORS

This invention relates to novel compounds and their use as pharmaceuticals particularly as Raf kinase inhibitors for the treatment of neurotraumatic diseases.

Raf protein kinases are key components of signal transduction pathways by which specific extracellular stimuli elicit precise cellular responses in mammalian cells. Activated cell surface receptors activate ras/rap proteins at the inner aspect of the plasmamembrane which in turn recruit and activate Raf proteins. Activated Raf proteins phosphorylate and activate the intracellular protein kinases MEK1 and MEK2. In turn, activated MEKs catalyse phosphorylation and activation of p42/p44 mitogen-activated protein kinase (MAPK). A variety of cytoplasmic and nuclear substrates of activated MAPK are known which directly or indirectly contribute to the cellular response to environmental change. Three distinct genes have been identified in mammals that encode Raf proteins; A-Raf, B-Raf and C-Raf (also known as Raf-1) and isoformic variants that result from differential splicing of mRNA are known.

Inhibitors of Raf kinases have been suggested for use in disruption of tumor cell growth and hence in the treatment of cancers, e.g. histiocytic lymphoma, lung adenocarcinoma, small cell lung cancer and pancreatic and breast carcinoma; and also in the treatment and/or prophylaxis of disorders associated with neuronal degeneration resulting from ischemic events, including cerebral ischemia after cardiac arrest, stroke and multi-infarct dementia and also after cerebral ischemic events such as those resulting from head injury, surgery and/or during childbirth.

We have now found a group of novel compounds that are inhibitors of Raf kinases, in particular inhibitors of B-Raf kinase.

According to the invention there is provided compounds of formula (I):

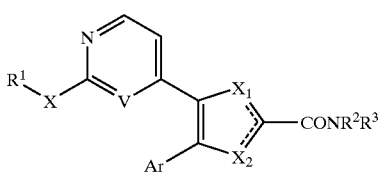

(I)

wherein
X is O, $CH_2$, S or NH, or the moiety X—$R^1$ is hydrogen;
V is CH or N;
$R^1$ is hydrogen, $C_{1-6}$alkyl, $C_{3-7}$cycloalkyl, aryl, aryl$C_{1-6}$alkyl, heterocyclyl, heterocyclyl$C_{1-6}$alkyl, heteroaryl, or heteroaryl$C_{1-6}$alkyl any of which, except hydrogen, may be optionally substituted;
$R^2$ and $R^3$ independently represent hydrogen, $C_{1-6}$alkyl, $C_{3-7}$cycloalkyl, aryl, aryl$C_{1-6}$alkyl, heteroaryl, heteroaryl$C_{1-6}$alkyl, heterocyclyl, or heterocyclyl$C_{1-6}$alkyl any one of which, except hydrogen, may be optionally substituted, or $R^2$ and $R^3$ together with the nitrogen atom to which they are attached form a 4- to 10-membered optionally substituted monocyclic or bicyclic ring;
Ar is an aryl or heteroaryl ring, either of which may be optionally substituted;
one of $X_1$ and $X_2$ is N and the other is $NR^4$, wherein $R^4$ is hydrogen, $C_{1-6}$alkyl, or aryl$C_{1-6}$alkyl;
or pharmaceutically acceptable salts thereof.

As used herein, the double bond indicated by the dotted lines of formula (I), represent the possible tautomeric ring forms of the compounds falling within the scope of this invention, the double bond being to the unsubstituted nitrogen atom.

Alkyl and alkenyl groups referred to herein, individually or as part of larger groups e.g. alkoxy, may be straight or branched groups containing up to six carbon atoms and are optionally substituted by one or more groups selected from the group consisting of aryl, heteroaryl, heterocyclyl, $C_{1-6}$alkoxy, $C_{1-6}$alkylthio, aryl$C_{1-6}$alkoxy, aryl$C_{1-6}$alkylthio, amino, mono- or di-$C_{1-6}$alkylamino, cycloalkyl, cycloalkenyl, carboxy and esters thereof, amide, sulphonamido, ureido, guanidino, $C_{1-6}$alkylguanidino, amidino, $C_{1-6}$alkylamidino, $C_{1-6}$acyloxy, azido, hydroxy, hydroxyimino and halogen. Preferably the optional substituent contains a solubilising group; suitable solubilising moieties will be apparent to those skilled in the art and include hydroxy and amine groups. Even more preferably the optional substituent include heterocyclyl e.g. piperidinyl, morpholinyl or piperazinyl, amino, mono- or di-$C_{1-6}$alkylamino, and hydroxy or any combination thereof.

Cycloalkyl and cycloalkenyl groups referred to herein include groups having from three to seven ring carbon atoms and are optionally substituted as described hereinabove for alkyl and alkenyl groups.

When used herein, the term "aryl" includes, unless otherwise defined, single and fused rings suitably containing from 4 to 7, preferably 5 or 6, ring atoms in each ring, which rings, may each be unsubstituted or substituted by, for example, up to three substituents.

Suitable aryl groups include phenyl and naphthyl such as 1-naphthyl or 2-naphthyl.

When used herein the term "heterocyclyl" includes, unless otherwise defined, non-aromatic, single and fused, rings suitably containing up to four heteroatoms in each ring, each of which is selected from O, N and S, which rings, may be unsubstituted or substituted by, for example, up to three substituents. Each heterocyclic ring suitably has from 4 to 7, preferably 5 or 6, ring atoms. A fused heterocyclic ring system may include carbocyclic rings and need include only one heterocyclic ring. Examples of heterocyclyl groups include pyrrolidine, piperidine, piperazine, morpholine, imidazolidine and pyrazolidine.

When used herein, the term "heteroaryl" includes, unless otherwise defined, mono- and bicyclic heteroaromatic ring systems comprising up to four, preferably 1 or 2, heteroatoms each selected from O, N and S. Each ring may have from 4 to 7, preferably 5 or 6, ring atoms. A bicyclic heteroaromatic ring system may include a carbocyclic ring. Examples of heteroaryl groups include pyrrole, quinoline, isoquinoline, pyridine, pyrimidine, oxazole, thiazole, thiadiazole, triazole, imidazole and benzimidazole.

Aryl, hererocyclyl and heteroaryl groups may be optionally substituted by preferably up to three substituents. Suitable substituents include halogen, $C_{1-6}$alkyl, aryl, aryl $C_{1-6}$alkyl, $C_{1-6}$alkoxy, $C_{1-6}$alkoxy $C_{1-6}$alkyl, halo $C_{1-6}$alkyl, aryl$C_{1-6}$alkoxy, hydroxy, nitro, cyano, azido, amino, mono- and di-N—$C_{1-6}$alkylamino, acylamino, arylcarbonylamino, acyloxy, carboxy, carboxy salts, carboxy esters, carbamoyl, mono- and di-N—$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, sulphonylamino, aminosulphonyl, $C_{1-6}$alkylthio, $C_{1-6}$alkylsulphinyl, $C_{1-6}$alkylsulphonyl, heterocyclyl, heteroaryl, heterocyclyl $C_{1-6}$alkyl, hydroxyimino-$C_{1-6}$alkyl and heteroaryl $C_{1-6}$alkyl and combinations thereof. Preferably the optional substituent contains a solubilising group; suitable solubilising moieties will be apparent to those skilled in the art and include hydroxy and amine groups. Even more preferably the optional substituent include heterocyclyl, amino, mono- or di-$C_{1-6}$alkylamino, amide, and hydroxy or any combination thereof.

X is preferably NH or X—$R^1$ is preferably hydrogen and when X is NH, $R^1$ is preferably hydrogen or $C_{1-6}$alkyl.

When V is CH, X—$R^1$ is preferably hydrogen.

When V is N, X—$R^1$ is preferably $NH_2$.

Most preferably X—$R^1$ is hydrogen.

Ar is preferably an optionally substituted phenyl.

Preferred substituents for the group Ar include halo, hydroxy, hydroxy $C_{1-6}$alkyl e.g. hydroxymethyl, hydroxyimino-$C_{1-6}$alkyl and $C_{1-6}$alkoxy e.g. methoxy. More preferred are halo and hydroxy. When Ar is phenyl the substituents are preferably present in the 3-position or the 3,4-positions. When Ar is phenyl it preferably has a 3-hydroxy or 3-chloro substituent, more preferably a 3-hydroxy substituent. Particular substitution patterns for Ar when phenyl are 3-hydroxy, 3-hydroxy-4-halo e.g. 3-hydroxy-4-chloro or 3-hydroxy-4-bromo, 3-hydroxy-4-methyl and 3-hydroxy-4-methoxy, more particularly 3-hydroxy-4-chloro.

Preferably $R^2$ and $R^3$ independently represent hydrogen, $C_{1-6}$alkyl, $C_{3-7}$cycloalkyl, aryl, aryl$C_{1-6}$alkyl, heteroaryl, heteroaryl$C_{1-6}$alkyl, heterocyclyl, or heterocyclyl$C_{1-6}$alkyl, or $R^2$ and $R^3$ together with the nitrogen atom to which they are attached form a 4- to 10-membered monocyclic or bicyclic ring.

Even more preferably $R^2$ and $R^3$ independently represent hydrogen, $C_{1-6}$alkyl, aryl, heteroaryl$C_{1-6}$alkyl, any of which except hydrogen can be optionally substituted or $R^2$ and $R^3$ together with the nitrogen atom to which they are attached form an optionally substituted 5 or 6 membered monocyclic or bicyclic ring for example piperidine.

The compounds of formula (I) preferably have a molecular weight of less than 800.

Particular compounds according to the invention include those mentioned in the examples and their pharmaceutically acceptable salts. It will be understood that the invention includes pharmaceutically acceptable derivatives of compounds of formula (I) and that these are included within the scope of the invention.

As used herein "pharmaceutically acceptable derivative" includes any pharmaceutically acceptable salt, ester or salt of such ester of a compound of formula (I) which, upon administration to the recipient, is capable of providing (directly or indirectly) a compound of formula (I) or an active metabolite or residue thereof.

It will be appreciated that for use in medicine the salts of the compounds of formula (I) should be pharmaceutically acceptable. Suitable pharmaceutically acceptable salts will be apparent to those skilled in the art and include those described in *J. Pharm. Sci.*, 1977, 66, 1–19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts e.g. oxalates, may be used, for example in the isolation of compounds of formula (I) and are included within the scope of this invention.

The compounds of this invention may be in crystalline or non-crystalline form, and, if crystalline, may optionally be hydrated or solvated. This invention includes within its scope stoichiometric hydrates as well as compounds containing variable amounts of water.

The invention extends to all isomeric forms including stereoisomers and geometric isomers of the compounds of formula (I) including enantiomers and mixtures thereof e.g. racemates. The different isomeric forms may be separated or resolved one from the other by conventional methods, or any given isomer may be obtained by conventional synthetic methods or by stereospecific or asymmetric syntheses.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

Compounds of formula (I) are imidazole derivatives which may be readily prepared using procedures well-known to those skilled in the art, and described in, for instance, Comprehensive Heterocyclic Chemistry, Editors Katritzky and Rees, Pergamon Press, 1984, 5, 457–497, from starting materials which are either commercially available or can be prepared from such by analogy with well-known processes. A key step in many such syntheses is the formation of the central imidazole nucleus. Suitable procedures are described in inter alia U.S. Pat. Nos. 3,707,475 and 3,940,486 which are herein incorporated by reference in their entirety. These patents describe the synthesis of α-diketones and α-hydroxyketones (benzoins) and their subsequent use in preparing imidazoles and N-hydroxyl imidazoles.

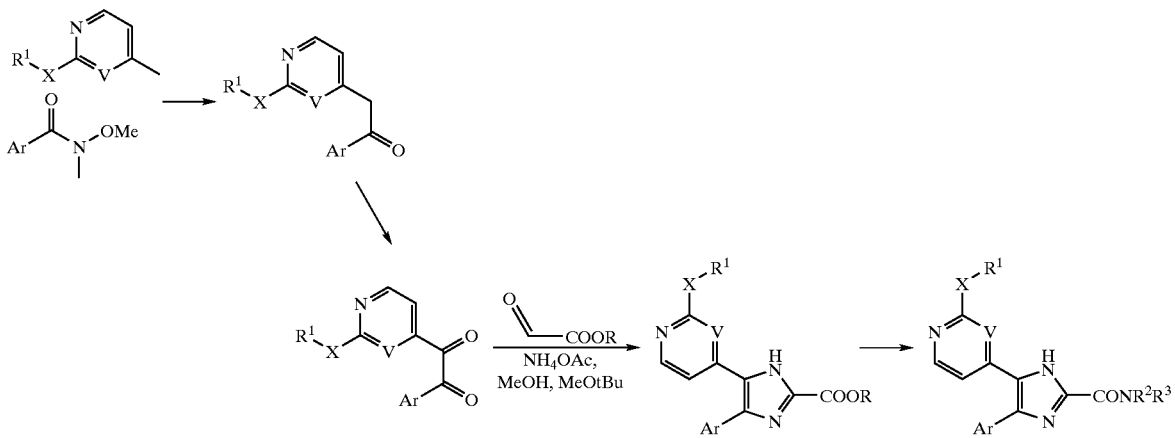

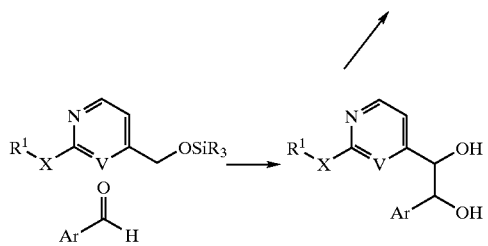

Preferred methods for preparing compounds of this invention are as outlined in the above scheme, wherein R is $C_{1-6}$alkyl or aryl$C_{1-6}$alkyl, preferably ethyl. α-Diketones are prepared by condensation of the anion of, for example, a 4-substituted pyridine derivative (V=CH, $R^1$—X=H) with the Weinreb amide of an aryl acid, or with an aryl-aldehyde, followed by oxidation of the intermediate product. Stirring the diketone with an aldehyde, such as glyoxylic acid ethyl ester, and ammonium acetate in a mixture of methanol and methyl-tert-butyl ether allows access to the imidazole nucleus, by analogy to the method described in patent WO 98/56788. Thereafter, the ethyl ester, the corresponding acid or an activated derivative thereof may be converted into an amide using conventional amide bond forming procedures. Such procedures are well known in the art and are described in, for instance, P. D. Bailey, I. D. Collier and K. M. Morgan in *Comprehensive Organic Functional Group Transformation*, Vol. 5, ed. C. J. Moody, p. 257, Elsevier Scientific, Oxford, 1995.

Non-selective alkylation of the imidazole nitrogen (using one of the procedures outlined in N. J. Liverton et al; *J. Med. Chem.*, 1999, 42, 2180–2190) with a compound of formula L-$R^4$ wherein L is a leaving group, e.g. halo, sulfonate or triflate, will yield both isomers of the compounds of formula (I) where $X_1$ or $X_2$ is $NR^4$ in which $R^4$ is other than hydrogen, the isomers can be separated by chromatographic methods.

During the synthesis of the compounds of formula (I) labile functional groups in the intermediate compounds, e.g. hydroxy, carboxy and amino groups, may be protected. A comprehensive discussion of the ways in which various labile functional groups may be protected and methods for cleaving the resulting protected derivatives is given in for example *Protective Groups in Organic Chemistry*, T. W. Greene and P. G. M. Wuts, (Wiley-Interscience, New York, 2nd edition, 1991).

The compounds of formula (I) may be prepared singly or as compound libraries comprising at least 2, for example 5 to 1,000 compounds, and more preferably 10 to 100 compounds of formula (I). Libraries of compounds of formula (I) may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I), or pharmaceutically acceptable salts thereof.

Pharmaceutically acceptable salts may be prepared conventionally by reaction with the appropriate acid or acid derivative.

The novel carboxylic esters and the corresponding acids of formula (II) which are used as intermediates in the synthesis of the compounds of formula (I) also form part of the present invention:

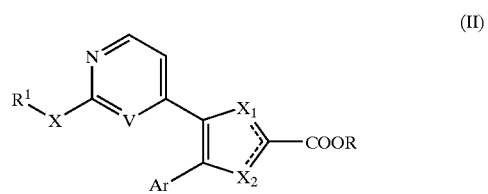

(II)

wherein X, V, $R^1$, Ar, $X_1$ and $X_2$ are as defined for formula (I) and R is hydrogen, $C_{1-6}$alkyl or aryl$C_{1-6}$alkyl.

As indicated above the compounds of formula (I) and their pharmaceutically acceptable salts are useful for the treatment and/or prophylaxis of disorders in which Raf kinases, in particular B-Raf kinase, are implicated.

According to a further aspect of the invention there is provided the use of a compound of formula (I) or a pharmaceutically acceptable salt thereof as an inhibitor of B-Raf kinase.

As indicated above the compounds of formula (I) and their pharmaceutically acceptable salts are useful the treatment and/or prophylaxis of disorders associated with neuronal degeneration resulting from ischemic events.

According to a further aspect of the invention there is provided a method of treatment or prophylaxis of a neurotraumatic disease, in a mammal in need thereof, which comprises administering to said mammal an effective amount of a compound of formula (I) or a pharmaceutically acceptable salt thereof.

According to a further aspect of the invention there is provided the use of a compound of formula (I) or a pharmaceutically acceptable salt thereof in the manufacture of a medicament for the prophylactic or therapeutic treatment of any disease state in a human, or other mammal, which is exacerbated or caused by a neurotraumatic event.

Neurotraumatic diseases/events as defined herein include both open or penetrating head trauma, such as caused by surgery, or a closed head trauma injury, such as caused by an injury to the head region. Also included within this definition is ischemic stroke, particularly to the brain area, transient ischemic attacks following coronary by-pass and cognitive decline following other transient ischemic conditions.

Ischemic stroke may be defined as a focal neurologic disorder that results from insufficient blood supply to a particular brain area, usually as a consequence of an embolus, thrombi, or local atheromatous closure of the blood vessel. Roles for stress stimuli (such as anoxia), redox injury, excessive neuronal excitatory stimulation and inflammatory cytokines in this area has been emerging and the present invention provides a means for the potential treatment of these injuries. Relatively little treatment, for an acute injury such as these has been available.

The compounds of the invention may also be used in the treatment or prophylaxis of cancers.

The compounds of the invention may also be of use for the treatment or prophylaxis of CSBP/p38 mediated diseases as described in WO 99/01131 and WO 99/01130.

It will be appreciated by those skilled in the art that reference herein to treatment extends to prophylaxis as well as the treatment of established infections or symptoms.

In order to use the compounds of formula (I) in therapy, they will normally be formulated into a pharmaceutical composition in accordance with standard pharmaceutical practice.

According to a further aspect of the invention there is provided a pharmaceutical composition comprising a compound of formula (I) or a pharmaceutically acceptable salt thereof and a pharmaceutically acceptable carrier.

The compounds of formula (I) may conveniently be administered by any of the routes conventionally used for drug administration, for instance, parenterally, orally, topically or by inhalation. The compounds of formula (I) may be administered in conventional dosage forms prepared by combining it with standard pharmaceutical carriers according to conventional procedures. The compounds of formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable carrier is dictated by the amount of compound of formula (I) with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. When a liquid carrier is used, the preparation will be in the form of a syrup, emulsion, soft gelatin capsule, sterile injectable liquid such as an ampoule or nonaqueous liquid suspension.

The compounds of formula (I) are preferably administered parenterally, that is by intravenous, intramuscular, subcutaneous intranasal, intrarectal, intravaginal or intraperitoneal administration. The intravenous form of parenteral administration is generally preferred. The compounds may be administered as a bolus or continuous infusion e.g. over 3 days. Appropriate dosage forms for such administration may be prepared by conventional techniques.

The compounds of formula (I) may also be administered orally. Appropriate dosage forms for such administration may be prepared by conventional techniques.

The compounds of formula (I) may also be administered by inhalation, that is by intranasal and oral inhalation administration. Appropriate dosage forms for such administration, such as aerosol formulations, may be prepared by conventional techniques.

The compounds of formula (I) may also be administered topically, that is by non-systemic administration. This includes the application of the inhibitors externally to the epidermis or the buccal cavity and the instillation of such a compound into the ear, eye and nose, such that the compound does not significantly enter the blood stream.

For all methods of use disclosed herein the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of the inhibitors will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of the inhibitors given per day for a defined number of days, can be ascertained by those skilled in the art using conventional course of treatment determination tests. In the case of pharmaceutically acceptable salts the above figures are calculated as the parent compound of formula (I).

No toxicological effects are indicated/expected when a compound of formula (I) is administered in the above mentioned dosage range.

AU publications, including but not limited to patents and patent applications, cited in this specification are herein incorporated by reference as if each individual publication were specifically and individually indicated to be incorporated by reference herein as though fully set forth.

The following Examples illustrate the preparation of pharmacologically active compounds of the invention and the following Descriptions illustrate the preparation of intermediates used in the preparation of these compounds.

Abbreviations used herein are as follows;
THF means tetrahydrofuran.

Description 1: 5-(3,4-Dichlorophenyl)-4-pyridin-4-yl-1H-imidazole-2-carboxylic acid ethyl ester Step 1. 1-(3,4-Dichlorophenyl)-2-pyridin-4-yl-ethane-1,2-diol 4-(tert-Butyldimethylsilyloxymethyl)-pyridine (T. F. Gallagher et al, *Bioorganic and Medicinal Chemistry;* 1997, 5, 49) (67 g, 0.3 mol) was dissolved in THF (250 ml) and cooled to −40° C. The solution was treated with a 2M solution of lithuim diisopropylamine in THF (200 ml, 0.4 mol) and stirred for 45 min maintaining a temperature of −40 to −20° C., before the dropwise addition of 3,4-dichlorobenzaldehyde (55.13 g, 0.32 mol) in THF (250 ml). The mixture was allowed to warm to room temperature then stirred for a further 18 hours. After re-cooling to 0° C. the reaction was quenched with saturated ammonium chloride solution (500 ml), and the resulting two phase mixture separated. The aqueous phase was extracted with ethyl acetate and the combined organics concentrated under reduced pressure. The residue was dissolved in ethyl acetate, washed with saturated sodium bicarbonate solution, water and brine, dried ($MgSO_4$) and concentrated under reduced pressure to an oil (129 g). The oil was dissolved in THF (300 ml) and a 1M solution of tetrabutylammonium fluoride (360 ml, 0.36 mol) added dropwise. The solution was stirred at room temperature for 45 min, then concentrated to an oil under reduced pressure. The oil was dissolved in ethyl acetate and washed with saturated sodium bicarbonate solution, water and brine, dried (MgSO$_4$) and evaporated under reduced pressure. The oil was triturated with hexane and the resulting solid filtered and washed with hexane to afford the title compound (67.58 g 79%) as a tan solid; MS(AP+) m/e 284/286/288 [M+H]+.

Step 2. 1-(3,4-Dichlorophenyl)-2-pyridin-4-yl-ethane-1,2-dione

Dimethylsulfoxide (37ml, 0.53 mol) was dissolved in dichloromethane (250 ml) and cooled to −78° C. Oxalyl chloride (34.5 ml, 0.40 mol) was added dropwise and the solution stirred for 20 min. A solution of the product of Step 1 (34 g, 0.12 mol) in dimethylsulfoxide (40 ml) and dichloromethane (200 ml) was added dropwise at −78° C., and the solution stirred for 30 min. Triethylamine (104 ml, 0.74 mol) was added dropwise and the solution became flocculent such that overhead stirring became necessary. The solution was allowed to stir at room temperature over 2 hours then was poured on to ice/saturated sodium bicarbonate solution. The aqueous layer was separated, and re-extracted with dichloromethane. The combined organic phases were concentrated under reduced pressure to a green-yellow solid. The solid was redissolved in dichloromethane and washed with water and brine, dried (MgSO$_4$) and evaporated to a solid. The crude solid was purified by silica gel chromatography eluting with dichloromethane, to afford the title compound (28.6 g, 85%) as a yellow solid; MS(-ve ion) m/e 279/281/283 [M−H]−.

Step 3. 5-(3,4-Dichlorophenyl)-4-pyridin-4-yl-1H-imidazole-2-carboxylic acid ethyl ester The product of Step 2 (2.0 g, 7.1 mmol) was dissolved in tert-butyl-methyl ether (50 ml). Glyoxylic acid ethyl ester (50% solution in toluene, 2.8 ml, 14.3 mmol) was then added followed by a solution of ammonium acetate (1.37 g, 17.8 mmol) in methanol (10 ml) which was added dropwise over 30 min. After stirring at room temperature overnight, the solvent was evaporated in vacuo, the residue dissolved in dichloromethane and then washed with aqueous potassium carbonate and brine. The organic layer was dried (MgSO$_4$), filtered and concentrated at reduced pressure. The residue was chromatographed on silica gel eluting with 5% of a 9:1 methanol: 0.880 ammonia solution, in ether to give the title compound as a pale yellow solid (600 mg, 23%); MS(AP+) m/e 362/364 [M+H]$^+$.

Description 2: 5-(3,4-Dichlorophenyl)-4-pyridin-4-yl-1H-imidazole-2-carboxylic acid D1 (520 mg, 1.4 mmol) was dissolved in methanol (10 ml), 40% aqueous sodium hydroxide solution (2 ml) added and the mixture heated to reflux overnight. On cooling, the solvent was removed in vacuo, the residue dissolved in water and washed with ether. The aqueous layer was cooled to 0° C. and acidified with acetic acid. The precipitate was filtered and dried under vacuum overnight to give the title compound, as a white solid (400 mg, 83%); MS(AP+) m/e 334 [M+H]$^+$.

Description 3: 5-(4-Chloro-3-methoxyphenyl)-4-pyridin-4-yl-1H-imidazole-2-carboxylic acid ethyl ester Step 1. 4-Chloro-3-,N-dimethoxy-N-methyl-benzamide A suspension of 4-chloro-3-methoxybenzoic acid (F. Claudi et al *J. Med. Chem.*, 1992, 35, 4408) (37.2 g, 0.2 mol) in dichloromethane (500 ml) containing oxalyl chloride (26 ml) was treated with N,N-dimethylformamide (10 drops). After stirring at room temperature for 6 hours the solution was concentrated at reduced pressure, additional dichloromethane was added to the residue and the solvent was re-evaporated. The residue was then dissolved in acetonitrile (600 ml) and methoxymethylamine hydrochloride (20.5 g, 0.21 mol) added. The mixture was cooled in an ice-bath, a solution of pyridine (80 ml) in acetonitrile (150 ml) added dropwise, and the mixture stirred at room temperature for 18 hours. The solution was concentrated and the residue partitioned between ethyl acetate and saturated potassium carbonate solution. The organic layer was separated, washed with brine, dried (MgSO$_4$) and concentrated at reduced pressure to give the title compound (40.0 g, 87%) as a colourless oil; MS(ES+) m/e 230/232 [M+H]+.

Step 2. 1-(4-Chloro-3-methoxy-phenyl)-2-pyridin4-yl-ethanone

4-Picoline (16.9 ml, 0.174 mol) was added dropwise to a stirred solution of lithium di-isopropylamide (110 ml, 0.22 mol, 2M solution in heptane, ethylbenzene, tetrahydrofuran) in dry tetrahydrofuran (150 ml) at −78° C. After stirring at −78° C. for 15 min a solution of the product of Step 1 (40.0 g, 0.174 mol) in tetrahydrofuran (100 ml) was added dropwise. The reaction was allowed to warm to room temperature over 3 hours. The solution was cooled in ice and saturated ammonium chloride solution added. The aqueous mixture was extracted with ethyl acetate, washed with brine, dried (MgSO$_4$), filtered and concentrated at reduced pressure. The resulting gum was triturated with cold diethyl ether/hexane (1:1, 300 ml) and the solid collected to give the title compound, as a pale yellow solid (29 g, 64%); MS(ES+) m/e 262/264 [M+H]+.

Step 3. 1-(4-Chloro-3-methoxy-phenyl)-2-pyridin-4-yl)-ethane-1,2-dione

A solution of the product of Step 2 (22.5 g, 86 mmol) in dimethylsulphoxide (150 ml) was stirred at 55° C. Hydrogen bromide (48% aqueous, 21 ml) was added dropwise and the solution maintained at 55° C. for 1 hour. After cooling to room temperature, the solution was poured into a solution of sodium acetate (21 g) in ice-water (1 litre) and the resulting slurry was stirred at room temperature for 30 min. The mixture was extracted with ethyl acetate and the organic layers were combined, washed with brine, dried (MgSO$_4$), filtered and concentrated at reduced pressure. The residue was triturated with diethyl ether/hexane (1:4) and the solid collected to give the title compound as a yellow solid; MS(EI) m/e 275/277 [M]+.

Step 4. 5-(4-Chloro-3-methoxyphenyl)-4-pyridin-4-yl-1H-imidazole-2-carboxylic acid ethyl ester The title compound (120 mg, 37%) was prepared from the product of Step 3 and glyoxylic acid ethyl ester using the method described in D1 Step 3; MS(ES+) m/e 358/360/362 [M+H]$^+$.

Description 4: 5-(4-Chloro-3-methoxyphenyl)-4-pyridin-4-yl-1H-imidazole-2-carboxylic acid The title compound (120 mg, 78%) was prepared from the product of D3 and aqueous sodium hydroxide, using the method described in D2; MS(AP−) m/e 328 [M−H]−.

EXAMPLE 1

1-[5-(3,4-Dichlorophenyl)-4-pyridin-4-yl-1H-imidazol-2-yl]-1-piperidin-1-yl-methanone Step 1. 5-(3,4-Dichlorophenyl)-4-pyridin-4-yl-1H-imidazole-2-carbonyl chloride D2 (360 mg, 1.1 mmol) was dissolved in dichloromethane (15 ml), oxalyl chloride (0.3 ml, 3.3 mmol) was added, followed by 1 drop of DMF, and the mixture stirred at room temperature for 1 h. The solvent was evaporated to give the title compound as a yellow solid which was used directly in the next step.

Step 2. 1-[5-(3,4-Dichlorophenyl)-4-pyridin-4-yl-1H-imidazol-2-yl]-1-piperidin-1-yl-methanone The product of Step 1 (52 mg, 0.15 mmol) was dissolved in anhydrous dichloromethane (3 ml), piperidine (0.025 ml, 0.23 mmol) was added followed by triethylamine (0.084 ml, 0.6 mmol) and the mixture stirred at room temperature for 2 hours. The mixture was diluted with dichloromethane and washed with aqueous sodium bicarbonate and brine. The organic layer was dried (MgSO$_4$) and evaporated under vacuum. The residue was chromatographed on silica gel eluting with 5% of a 9:1 methanol:0.880 ammonia solution, in dichloromethane to give the title compound as a white solid (16 mg, 26%); MS(AP+) m/e 402 [M+H]$^+$.

EXAMPLE 2

5-(4-Chloro-3-methoxyphenyl)-4-pyridin-4-yl-1H-imidazol-2-yl]-1-piperidin-1-yl-methanone Step 1. 5-(4-Chloro-3-methoxyphenyl)-4-pyridin-4-yl-1H-imidazole-2-carbonyl chloride The title compound was prepared from the product of D4 using the method described in Example 1 Step 1.

Step 2. 5-(4-Chloro-3-methoxyphenyl)-4-pyridin-4-yl-1H-imidazol-2-yl]-1-piperidin-1-yl-methanone The title compound (30 mg, 50%) was prepared from the product of Step 1 and piperidine using the method described in Example 1, Step 2: MS(AP+) m/e 397/399 [M+H]$^+$.

EXAMPLE 3

1-[5-(4-Chloro-3-hydroxyphenyl)-4-pyridin-4-yl-1H-imidazol-2-yl]-1-piperidin-1-yl-methanone A solution of Example 2 (18 mg, 0.045 mmol) in dichloromethane (5 ml) was cooled to 0° C. and treated with boron tribromide (1M in dichloromethane, 0.14 ml, 0.14 mmol). The solution was stirred at 0° C. for 1 hour then at room temperature for a further 5 hours. 2M Hydrochloric acid (1 ml) was added and the reaction heated to 50° C. for 1 hour. After cooling, the mixture was basified with potassium carbonate solution and the resultant precipitate collected by filtration. The residue was chromatographed on silica gel eluting with 10% of a 9:1 methanol:0.880 ammonia solution, in dichloromethane to give the title compound as a white solid (10 mg, 58%); MS(AP+) m/e 383/385 [M+H]$^+$.

The following examples were prepared by the general two-step method described in Example 1.

| Example | Amine | Characterisation |
|---|---|---|
| 4 | 5-(3,4-Dichlorophenyl)-4-pyridin-4-yl-1H-imidazole-2-carboxylic acid (3-dimethylamino-propyl)-amide | 3-Dimethyl propylamine | MS(AP+) m/e 418/420 [M + H]$^+$ |
| 5 | 3-({1-[5-(3,4-Dichlorophenyl)-4-pyridin-4-yl-1H-imidazol-2-yl]-methanoyl}-amino)-propionic acid tert-butyl ester | 3-Amino-propionic acid tert-butyl ester | MS(AP+) m/e 462/464 [M + H]$^+$ |
| 6 | 3-({1-[5-(3,4-Dichlorophenyl)-4-pyridin-4-yl-1H-imidazol-2-yl]-methanoyl}-amino)-propionic acid | 4-Amino-propionic acid | MS(AP+) m/e 405/407 [M + H]$^+$ |
| 7 | 5-(3,4-Dichlorophenyl)-4-pyridin-4-yl-1H-imidazole-2-carboxylic acid [2-(1H-indol-3-yl)-ethyl]-amide | 2-(1H-Indol-3-yl)-ethylamine | MS(AP+) m/e 476/478 [M + H]$^+$ |
| 8 | 5-(3,4-Dichlorophenyl)-4-pyridin-4-yl-1H-imidazole-2-carboxylic acid (4-morpholin-4-yl-phenyl)-amide | 4-Morpholin-4-yl-phenylamine | MS(AP+) m/e 497 [M + H]$^+$ |

The following examples were prepared by the general two-step method described in Example 2.

| Example | Amine | Characterisation |
|---|---|---|
| 9 | 5-(4-Chloro-3-methoxyphenyl)-4-pyridin-4-yl-1H-imidazole-2-carboxylic acid (3-dimethylamino-propyl)-amide | 3-Dimethyl aminopropyl amine | MS(AP+) m/e 415/417 [M + H]$^+$ |

The following examples were prepared by the general method described in Example 3.

| Example | Precursor | Characterisation |
|---|---|---|
| 10 | 5-(4-Chloro-3-hydroxyphenyl)-4-pyridin-4-yl-1H-imidazole-2-carboxylic acid (3-dimethylamino-propyl)-amide | Example 9 | MS(AP+) m/e 400/402 [M + H]$^+$ |

EXAMPLE 11

5-(4-chloro-3-hydroxyphenyl)-4-pyridin-4-yl-1H-imidazole-2-carboxylic acid (2-dimethylamino ethyl) amide Step 1. 5-(4-Chloro-3-hydroxyphenyl)-4-pyridin-4-yl-1H-imidazole-2-carboxylic acid.

D3 (7.60 g, 21 mmol) was suspended in dichloromethane (200 ml) and treated with a 1 molar solution of boron tribromide in dichloromethane (100 ml, 100 mmol). The suspension was stirred at room temperature for 16 hours, 5M hydrochloric acid (50 ml) added and the mixture heated at reflux for a further 30 minutes. The mixture was then concentrated and the pH adjusted to ca. pH11 with 40% sodium hydroxide solution. The solution was warmed to 50° C. to complete ester hydrolysis and the product precipitated by acidification to pH4–5 with acetic acid. The solid was filtered, washed water and ether then dried under vacuum to afford the title compound (3.67 g, 55%); MS(AP+) m/e 315/317 [M+H]$^+$ Step 2. 5-(4-Chloro-3-hydroxyphenyl)-4-pyridin-4-yl-1H-imidazole-2-carbonyl chloride A suspension of the product from Step 1 (1.24 g, 3.9 mmol) in dichloromethane (50 ml) was treated with oxalyl chloride (3.4 ml, 39 mmol) and 10 drops dimethylformamide. The suspension was then heated at reflux for 5 hours, cooled and concentrated under vacuum. The resultant residue was azeotroped with toluene then trituated with hexane to afford the title compound (1.56 g), which was used without further purification.

Step 3. 5-(4-chloro-3-hydroxyphenyl)-4-pyridin-4-yl-1H-imidazole-2-carboxylic acid (2-dimethylamino ethyl) amide The product from Step 2 (124 mg, 0.3 mmol) was suspended in dichioromethane (5 ml) and treated with a solution of N,N-dimethyl ethylenediamine (0.036 ml, 0.33 mmol), and triethylamine (0.125 ml, 0.9 mmol) in dichloromethane (1 ml). The reaction mixture was then stirred at room temperature overnight, washed saturated sodium bicarbonate solution (3 ml) and passed through a Varain Chem Elut hydromatric cartridge to remove the aqueous phase. The filtrate was then concentrated and purified by silica gel chromatography, eluting with 0.3:3:7 dichloromethane: ethanol:0.880 ammonia solution to afford the title compound (20 mg, 17%); MS(AP+) m/e 386/388 [M+H]$^+$ The following examples were prepared by the general method described in Example 11.

| Example | | Amine | Characterisation |
|---|---|---|---|
| 12 | 5-(4-chloro-3-hydroxy-phenyl)-4-pyridin-4-yl-1H-imidazole-2-carboxylic acid (3-piperidin-1-yl-propyl) amide | 3-(piperidin-1-yl)-propylamine | MS(AP+) m/e 440/442 [M + H]+ |
| 13 | 5-(4-chloro-3-hydroxyphenyl)-4-pyridin-4-yl-1H-imidazole-2-carboxylic acid (3-dimethylamino-2-dimethylpropyl) amide | N,N,-2,2-tetramethyl-propane-1,3-diamine | MS(AP+) m/e 428/430 [M + H]+ |
| 14 | 5-(4-chloro-3-hydroxyphenyl)-4-pyridin-4-yl-1H-imidazole-2-carboxylic acid (4-benzyl-piperazin-1-yl) amide | N-benzyl piperazine | MS(AP+) m/e 474/476 [M + H]+ |

It is to be understood that the present inventions covers all combinations of particular and preferred subgroups described hereinabove.

BIOLOGICAL EXAMPLES

The activity of compounds of formula (I) as B-Raf inhibitors may be determined by the following in vitro assays:

Fluorescence Anisotropy Kinase Binding Assay

The kinase enzyme, fluorescent ligand and a variable concentration of test compound are incubated together to reach thermodynamic equilibrium under conditions such that in the absence of test compound the fluorescent ligand is significantly (>50%) enzyme bound and in the presence of a sufficient concentration (>10×$K_i$) of a potent inhibitor the anisotropy of the unbound fluorescent ligand is measurably different from the bound value.

The concentration of kinase enzyme should preferably be ≧1×$K_f$. The concentration of fluorescent ligand required will depend on the instrumentation used, and the fluorescent and physicochemical properties. The concentration used must be lower than the concentration of kinase enzyme, and preferably less than half the kinase enzyme concentration. A typical protocol is:

All components dissolved in Buffer of composition 50 mM HEPES, pH 7.5, 1 mM CHAPS, 10 mM $MgCL_2$.

B-Raf Enzyme concentration: 1 nM

Fluorescent ligand concentration: 0.5 nM

Test compound concentration: 0.1 nM–100 uM

Components incubated in 10 ul final volume in LJL HE 384 type B black microtitre plate until equilibrium reached (Over 3 h, up to 30 h)

Fluorescence anisotropy read in LJL Acquest.

Definitions: $K_i$=dissociation constant for inhibitor binding $K_f$=dissociation constant for fluorescent ligand binding The fluorescent ligand is the following compound:

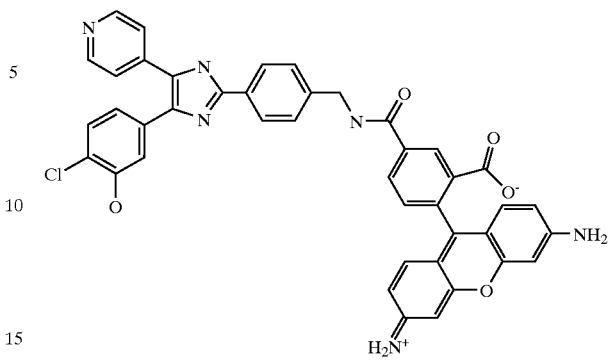

which is derived from 5-[2-(4-aminomethylphenyl)-5-pyridin-4-yl-1H-imidazol-4-yl]-2-chlorophenol and rhodamine green.

Raf Kinase Assay

Activity of human recombinant B-Raf protein was assessed in vitro by assay of the incorporation of radiolabelled phosphate to recombinant MAP kinase (MEK), a known physiologic substrate of B-Raf. Catalytically active human recombinant B-Raf protein was obtained by purification from sf9 insect cells infected with a human B-Raf recombinant baculovirus expression vector. To ensure that all substrate phosphorylation resulted from B-Raf activity, a catalytically inactive form of MEK was utilised. This protein was purified from bacterial cells expression mutant inactive MEK as a fusion protein with glutathione-S-transfcrase (GST-kdMEK).

Method: Standard assay conditions of B-Raf catalytic activity utilised 3 ug of GST-kdMBK, 10 uM ATP and 2 uCi $^{33}$P-ATP, 50 mM MOPS, 0.1 mM EDTA, 0.1M sucrose, 10 mM $MgCl_2$ plus 0.1% dimethylsulphoxide (containing compound where appropriate) in a total reaction volume of 30 ul. Reactions were incubated at 25° C. for 90 minutes and reactions terminated by addition of EDTA to a final concentration of 50 uM. 10 ul of reaction was spotted to P30 phosphocellulose paper and air dried. Following four washes in ice cold 10% trichloroacetic acid, 0.5% phosphoric acid, papers were air dried prior to addition of liquid scintillant and measurement of radioactvity in a scintillation counter.

Results: The compounds of the examples were found to be effective in either of the above assays having $K_d$'s (in the case of the binding assay) or $IC_{50}$'s (in the kinase assay) of <3 μM.

The activity of compounds as Raf inhibitors may also be determined by the assays described in WO 99/10325; McDonald, O. B., Chen, W. J., Ellis, B., Hoffman, C., Overton, L., Rink, M., Smith, A., Marshall, C. J. and Wood, E. R. (1999) A scintillation proximity assay for the Raf/MEK/ERK kinase cascade: high throughput screening and identification of selective enzyme inhibitors, Anal. Biochem. 268: 318–329 and AACR meeting New Orleans 1998 Poster 3793.

The neuroprotective properties of B-Raf inhibitors may be determined by the following in vitro assay:

Neuroprotective Properties of B-Raf Inhibitors in Rat Hippocampal Slice Cultures Organotypic cultures provide an intermediate between dissociated neuronal cell cultures and in-vivo models of oxygen and glucose deprivation (OGD). The majority of glial-neuronal interactions and neuronal circuitry are maintained in cultured Hippocampal slices, so facilitating investigation of the patterns of death among differing cell types in a model that resembles the in vivo situation. These cultures allow the study of delayed cellular damage and death 24 hours, or more, post-insult and permit assessment of the consequences of long-term alterations in culture conditions. A number of laboratories have reported delayed neuronal damage in response to OGD in organotypic cultures of the hippocampus (Vornov et al., *Stroke*, 1994, 25, 57–465; Newell et al., *Brain Res.*, 1995, 676, 38–44). Several classes of compounds have been shown to protect in this model, including EAA antagonists (Strasser et al., *Brain Res.*, 1995, 687, 167–174), Na channel blockers (Tasker et al., *J. Neurosci.*, 1992, 12, 98–4308) and Ca channel blockers (Pringle et al., *Stroke*, 1996, 7, 2124–2130). To date, relatively little is known of the roles of intracellular kinase mediated signalling pathways in neuronal cell death in this model.

Method: Organotypic hippocampal slice cultures were prepared using the method of Stoppini et al., *J. Neurosci. Methods*, 1995, 37, 173–182. Briefly, 400 micron sections prepared from hippocampi of 7–8 day postnatal Sprague Dawley rats are cultured on semiporous membranes for 9–12 days. OGD is then induced by incubation in serum and glucose-free medium in an anaerobic chamber for 45 minutes. Cultures are then returned to the air/$CO_2$ incubator for 23 hours before analysis. Propidium iodide (PI) is used as an indicator of cell death. PI is non toxic to neurones and has been used in many studies to ascertain cell viability. In damaged neurons PI enters and binds to nucleic acids. Bound PI shows increased emission at 635 nm when excited at 540 nm. One PI fluorescence image and one white light image are taken and the proportion of cell death analysed. The area of region CA1 is defined from the white light image and superimposed over the PI image. The PI signal is thresholded and area of PI damage expressed as a percentage of the CA1 area. Correlation between PI fluorescence and histologically confirmed cell death has been validated previously by Nissl-staining using cresyl fast violet (Newell et al., *J. Neurosci.*, 1995, 15, 7702–7711).

It is to be understood that the present invention covers all combinations of particular and preferred groups described herein above.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

What is claimed is:

1. A compound of formula (I):

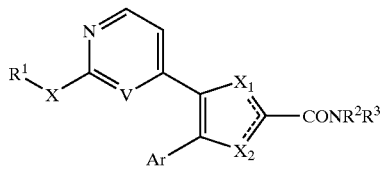

wherein
X is O, $CH_2$, S or NH, or the moiety X—$R^1$ is hydrogen;
V is CH or N;
$R^1$ is hydrogen, $C_{1-6}$alkyl, $C_{3-7}$cycloalkyl, aryl, aryl$C_{1-6}$alkyl, heterocyclyl, heterocyclyl$C_{1-6}$alkyl, heteroaryl or heteroaryl$C_{1-6}$alkyl any of which except hydrogen may be optionally substituted;

$R^2$ and $R^3$ independently represent hydrogen, $C_{1-6}$alkyl, $C_{3-7}$cycloalkyl, aryl, aryl$C_{1-6}$alkyl, heteroaryl, heteroaryl$C_{1-6}$alkyl, heterocyclyl, or heterocyclyl$C_{1-6}$alkyl any one of which except hydrogen may be optionally substituted, or $R^2$ and $R^3$ together with the nitrogen atom to which they are attached form a 4- to 10-membered optionally substituted monocyclic or bicyclic ring;

Ar is an aryl or heteroaryl ring either of which may be optionally substituted;

one of $X_1$ and $X_2$ is N and the other is $NR^4$, wherein $R^4$ is hydrogen, $C_{1-6}$alkyl, or aryl$C_{1-6}$alkyl;

or a pharmaceutically acceptable salt thereof.

2. A compound according to claim 1 wherein X—$R^1$ is hydrogen.

3. A compound according to claim 1 wherein Ar is optionally substituted phenyl.

4. A compound according to claim 3 wherein Ar is substituted by up to 3 substituents independently selected from halo, hydroxy, hydroxy $C_{1-6}$alkyl, hydroxyimino $C_{1-6}$alkyl, and $C_{1-6}$alkoxy.

5. A compound as claimed in claim 1 wherein $R^2$ and $R^3$ independently represent hydrogen, $C_{1-6}$alkyl, aryl, heteroaryl$C_{1-6}$alkyl, any of which except hydrogen can be optionally substituted, or $R^2$ and $R^3$ together with the nitrogen atom to which they are attached form an optionally substituted 5 or 6 membered monocyclic or bicyclic ring for example piperidine.

6. A compound which is:
1-[5-(3,4-Dichlorophenyl)-4-pyridin-4-yl-1H-imidazol-2-yl]-1-piperidin-1-yl-methanone;
5-(4-Chloro-3-methoxyphenyl)-4-pyridin-4-yl-1H-imidazol-2-yl]-1-piperidin-1-yl-methanone;
1-[5-(4-Chloro-3-hydroxyphenyl)-4-pyridin-4-yl-1H-imidazol-2-yl]-1-piperidin-1-yl-methanone;
5-(3,4-Dichlorophenyl)-4-pyridin-4-yl-1H-imidazole-2-carboxylic acid (3-dimethylamino-propyl)-amide;
3-({1-[5-(3,4-Dichlorophenyl)-4-pyridin-4-yl-1H-imidazol-2-yl]-methanoyl}-amino)-propionic acid tert-butyl ester;
3-({1-[5-(3,4-Dichlorophenyl)-4-pyridin-4-yl-1H-imidazol-2-yl]-methanoyl}amino)-propionic acid;
5-(3,4-Dichlorophenyl)-4-pyridin-4-yl-1H-imidazole-2-carboxylic acid [2-(1H-indol-3-yl)-ethyl]-amide;
5-(3,4-Dichlorophenyl)-4-pyridin-4-yl-1H-imidazole-2-carboxylic acid (4-morpholin-4-yl-phenyl)-amide;
5-(4-Chloro-3-methoxyphenyl)-4-pyridin-4-yl-1H-imidazole-2-carboxylic acid (3-dimethylamino-propyl)-amide;
5-(4-Chloro-3-hydroxyphenyl)-4-pyridin-4-yl-1H-imidazole-2-carboxylic acid (3-dimethylamino-propyl)-amide;
5-(4-chloro-3-hydroxyphenyl)-4-pyridin-4-yl-1H-imidazole-2-carboxylic acid (2-dimethylamino ethyl) amide;
5-(4-chloro-3-hydroxy-phenyl)-4-pyridin-4-yl1H-imidazole-2-carboxylic acid (3-piperidin-1-yl-propyl) amide; or
5-(4-chloro-3-hydroxyphenyl)-4-pyridin-4-yl-1H-imidazole-2-carboxylic acid (3-dimethylamino-2-dimethylpropyl) amide.

7. A pharmaceutical composition comprising a compound according to claim 1 or a pharmaceutically acceptable salt thereof and a pharmaceutically acceptable carrier.

8. A compound of formula (II):

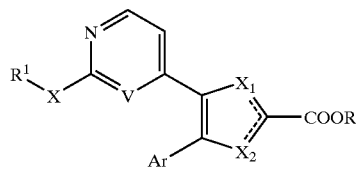

(II)

wherein X, V, R¹, Ar, X₁ and X₂ are as defined for formula (I) and R is hydrogen, $C_{1-6}$alkyl or aryl$C_{1-6}$alkyl.

9. A method for therapeutic treatment of open or penetrating head trauma, ischemic stroke, transient ischemic attacks in a human, or other mammal, which is exacerbated or caused by a neurotraumatic event, comprising administering to said human or mammal, an effective amount of a compound according to claim 1 or a pharmaceutically acceptable salt thereof.

* * * * *